(12) United States Patent
Freishtat et al.

(10) Patent No.: US 12,377,120 B2
(45) Date of Patent: Aug. 5, 2025

(54) EXOSOMES AND METHODS OF USE THEREOF

(71) Applicant: CHILDREN'S NATIONAL MEDICAL CENTER, Washington, DC (US)

(72) Inventors: Robert J. Freishtat, Potomac, MD (US); Evan P. Nadler, Washington, DC (US)

(73) Assignee: CHILDREN'S NATIONAL MEDICAL CENTER, Washington, DC (US)

(*) Notice: Subject to any disclaimer, the term of this patent is extended or adjusted under 35 U.S.C. 154(b) by 1162 days.

(21) Appl. No.: 16/628,306

(22) PCT Filed: Jul. 6, 2018

(86) PCT No.: PCT/US2018/041020
§ 371 (c)(1),
(2) Date: Jan. 3, 2020

(87) PCT Pub. No.: WO2019/010373
PCT Pub. Date: Jan. 10, 2019

(65) Prior Publication Data
US 2020/0215120 A1    Jul. 9, 2020

Related U.S. Application Data

(60) Provisional application No. 62/529,093, filed on Jul. 6, 2017.

(51) Int. Cl.
*A61K 35/35* (2015.01)
*A61K 38/17* (2006.01)
*A61K 9/00* (2006.01)
*C12N 15/63* (2006.01)

(52) U.S. Cl.
CPC .......... *A61K 35/35* (2013.01); *A61K 38/1709* (2013.01); *A61K 9/0019* (2013.01); *C12N 15/63* (2013.01)

(58) Field of Classification Search
None
See application file for complete search history.

(56) References Cited

U.S. PATENT DOCUMENTS

| 8,637,254 B2 | 1/2014 | Taylor et al. |
| 2006/0116321 A1* | 6/2006 | Robbins ................. A61P 37/08 514/7.3 |
| 2012/0134998 A1 | 5/2012 | Hotamisligil et al. |
| 2013/0195899 A1 | 8/2013 | Ichim et al. |

(Continued)

FOREIGN PATENT DOCUMENTS

| WO | 2013/048734 A1 | 4/2013 |
| WO | 2016/033695 A1 | 3/2016 |

(Continued)

OTHER PUBLICATIONS

Tarnopolsky et al., Mol. Genet. Metabolism 117(2): S112 (2016).*

(Continued)

*Primary Examiner* — Erin M. Bowers
(74) *Attorney, Agent, or Firm* — Robert C. Netter, Jr.; Dann, Dorfman, Herrell & Skillman (57) ABSTRACT

Exosomes, particularly adipocyte-derived exosomes, and methods of use thereof are provided.

13 Claims, 1 Drawing Sheet

(56) References Cited

U.S. PATENT DOCUMENTS

2014/0065240 A1 3/2014 Mitsialis et al.
2018/0136230 A1 5/2018 Freishtat et al.

FOREIGN PATENT DOCUMENTS

| WO | | 2016/044947 | A1 | | 3/2016 |
|---|---|---|---|---|---|
| WO | | 2016/123556 | A1 | | 8/2016 |
| WO | WO | 2016/123556 | | * | 8/2016 |
| WO | | 2016/201220 | A1 | | 12/2016 |
| WO | | 2017/194499 | A1 | | 11/2017 |
| WO | | 2018/045022 | A1 | | 3/2018 |
| WO | | 2018/089901 | A2 | | 5/2018 |

OTHER PUBLICATIONS

Lee et al., Protein J. 34: 230-235 (2015).*
Ferrante et al., Pediatr. Res. 77(3): 447-454 (2015).*
Momen-Heravi et al., Biol. Chem. 394(10): 1253-1262 (2013).*
Thoidis, G., et al., "Immunological analysis of GLUT4-enriched vesicles. Identification of novel proteins regulated by insulin and diabetes" J. Biol. Chem. (1993) 268(16):11691-6.
Anonymous, "FABP4/Ap2 Antibody (C-terminus, Magnetic Beads) LS-C171962" LSBio, retrieved from the Internet on Oct. 5, 2018: https://www.lsbio.com/antibodies/fabp4-antibody-ap2-antibody-c-terminus-magnetic-beads-ip-ls-c171962/179363.
Lee, J.E., et al., "Proteomic Analysis of Extracellular Vesicles Released by Adipocytes of Otsuka Long-Evans Tokushima Fatty (OLETF) Rats" Protein J. (2015) 34(3):220-35.
Ferrante, S., et al., "Adipocyte Exosomal miRNAs may Mediate the Effects of Obesity on Lung Disease" J. Invest. Med. (2013) 61(3):666-667.
Rome, S., "Are extracellular microRNAs involved in type 2 diabetes and related pathologies?" Clin. Biochem. (2013) 46(10-11):937-45.
Karolina, D.S., et al., "Circulating miRNA profiles in patients with metabolic syndrome" J. Clin. Endocrinol. Metab. (2012) 97(12):E2271-6.
Kranendonk, M.E., et al., "Extracellular vesicle markers in relation to obesity and metabolic complications in patients with manifest cardiovascular disease" Cardiovasc. Diabetol. (2014) 13:37.
Hubal, M.J., et al., "Circulating adipocyte-derived exosomal MicroRNAs associated with decreased insulin resistance after gastric bypass" Obesity (2017) 25(1):102-110.
Ferrante, S.C., et al., "Adipocyte-derived Exosomal miRNAs: A Novel Mechanism for Obesity-Related Disease" Pediatr. Res. (2015) 77(3): 447-454.
Deng, Z.B., et al., "Adipose Tissue Exosome-Like Vesicles Mediate Activation of Macrophage-Induced Insulin Resistance" Diabetes (2009) 58:2498-2505.
Camussi, G., et al., "Exosome/microvesicle-mediated epigenetic reprogramming of cells" Am. J. Cancer Res. (2011) 1(1):98-110.
Koeck, E.S., et al., "Adipocyte exosomes induce transforming growth factor beta pathway dysregulation in hepatocytes: a novel paradigm for obesity-related liver disease" J. Surg. Res. (2014) 192(2):268-75.
Ussar, S., et al., "Asc-1, PAT2 and P2RX5 are novel cell surface markers for white, beige and brown adipocytes" Sci. Transl. Med. (2014) 6(247):247ra103.

Khalyfa, A., et al., "Circulating Plasma Extracellular Microvesicle MicroRNA Cargo and Endothelial Dysfunction in Children with Obstructive Sleep Apnea" Am. J. Respir. Crit. Care Med. (2016) 194(9):1116-1126.
Kishida, K., et al., "Visceral adiposity as a target for the management of the metabolic syndrome" Annals of Medicine (2012) 44:233-241.
Zernecke, A et al., "Delivery of MicroRNA-126 by Apoptotic Bodies Induces CXCL12-Dependent Vascular Protection" Science Signaling (2009) 2(100):ra81.
Xu, A., et al., "Adipocyte fatty acid-binding protein is a plasma biomarker closely associated with obesity and metabolic syndrome" Clin. Chem. (2006) 52(3):405-13.
Momen-Heravi, F., et al., "Current Methods for the Isolation of Extracellular Vesicles" Bio. Chem. (2013) 394(10):1253-1262.
Witwer, K.W., et al., "Standardization of Sample Collection and Analysis Methods in Extracellular Vesicle Research" J. Extracellular Vesicles (2013) 2:20360.
Vlassov, A.V., et al., "Exosomes: Current Knowledge of Their Composition, Biological Functions, and Diagnostic and Therapeutic Potentials" Biochimica et Biophysica Acta (2012) 1820:940-948.
National Institutes of Health, "The Practical Guide: Identification, Evaluation, and Treatment of Overweight and Obesity in Adults" NIH Publication No. 00-4084 (2013) pp. 1-80.
Ertunc, M.E., et al., "Secretion of Fatty Acid Binding Protein aP2 from Adipocytes through a Nonclassical Pathway in Response to Adipocyte Lipase Activity" Journal Lipid Research (2015) 56:423-434.
Andaloussi, S.E., et al., "Exosomes for Targeted siRNA Delivery Across Biological Barriers" Adv. Drug Delivery Rev. (2012) 65:391-397.
Tarnopolsky, M., et al., "Exosome-mRNA and Exosome-Protein Therapy for Niemann-Pick Disease Type C" Mol. Genetics Metabolism (2016) 117(2):S112.
Thomou, T., et al., "Adipose-derived Circulating miRNAs Regulate Gene Expression in Other Tissues" Nature (2017) 542:450-455.
Johnsen, K.B., et al., "Evaluation of Electroporation-induced Adverse Effects on Adipose-derived Stem Cell Exosomes" Cytotechnology (2016) 68:2125-2138.
Hubal, M.J., et al., "Circulating Adipocyte-Derived Exosomal MicroRNAs Associated with Decreased Insulin Resistance After Gastric Bypass" Obesity (2017) 25:102-110.
Herrera, B.M., et al., "Global microRNA expression profiles in insulin target tissues in a spontaneous rat model of type 2 diabetes" Diabetologia (2010) 53:1099-1109.
Davalos, A., et al., "miR-33a/b contribute to the regulation of fatty acid metabolism and insulin signaling" PNAS (2011) 108:9232-9237.
Higuchi, C., et al., "Identification of Circulating miR-101, miR-375 and miR-802 as Biomarkers for Type 2 Diabetes" Metab. Clin. Exper. (2015) 64:489-497.
Connolly, et al., "Characterisation of adipocyte-derived extracellular vesicles released pre- and post-adipogenesis" J. Extracell. Vesicles (2015) 4:29159.
Shan, et al., "Fatty acid binding protein 4 expression marks a population of adipocyte progenitors in white and brown adipose tissues" FASEB J. (2013) 27(1):277-87.

* cited by examiner

EXOSOMES AND METHODS OF USE THEREOF

This application is a § 371 application of PCT/US2018/041020, filed Jul. 6, 2018, which claims priority under 35 U.S.C. § 119 (e) to U.S. Provisional Patent Application No. 62/529,093, filed on Jul. 6, 2017. The foregoing applications are incorporated by reference herein.

FIELD OF THE INVENTION

The present invention relates to the delivery of compounds to cells or a subject including in vivo delivery across biological membranes such as the blood-brain barrier.

BACKGROUND OF THE INVENTION

In the more than years since the start of the human genome project, thousands of single gene disorders have been identified affecting ~24 million Americans. However, treatments exist for only a handful of these diseases. While 20 gene (DNA) and/or gene product (e.g., mRNA, cDNA, or protein) replacement is often successful in vitro, in vivo delivery frequently fails due to delivery vehicle (e.g. virus, nanoparticle, etc.) inadequacies, immunogenicity, and/or tumorigenicity (Yla-Herttuala, S., Mol. Ther. (2015) 23:1551-2). Moreover, few—if any—gene transfer technologies can successfully target multiple tissues (Cox, et al., Nat. Med. (2015) 21:121-31). Improved methods of delivery are needed.

SUMMARY OF THE INVENTION

In accordance with one aspect of the instant invention, methods of delivering a compound to a cell are provided. In a particular embodiment, the method comprises contacting the cell with exosomes, particularly adipose or adipocyte-derived exosomes, containing the compound. In a particular embodiment, the cell is in a subject (e.g., in vivo administration) and the exosomes are from the subject to be administered the compound. In a particular embodiment, the method comprises isolating the exosomes (e.g., adipocyte-derived exosomes) from a biological sample from a subject and adding the compound to the exosomes.

In accordance with another aspect of the instant invention, methods of delivering a compound to a subject (e.g., an ex vivo method), including across the blood brain barrier of a subject, are provided. In a particular embodiment, the method comprises administering exosomes, such as adipocyte-derived exosomes, containing the compound to the subject. In a particular embodiment, the exosomes are from the subject to be administered the compound. In a particular embodiment, the exosomes are administered to the bloodstream of the subject (e.g., by injection or across mucosa (e.g., intranasally)). In a particular embodiment, the method further comprises isolating the adipocyte-derived exosomes from a biological sample from the subject and adding the compound to the exosomes.

In accordance with another aspect of the instant invention, methods for inhibiting, treating, and/or preventing a disease or disorder are provided. In a particular embodiment, methods of treating Niemann Pick disease are provided. In a particular embodiment, the method comprises administering exosomes, such as adipocyte-derived exosomes, containing Niemann-Pick disease, type C1 (NPC1) or a nucleic acid molecule encoding NPC1 to the subject. In a particular embodiment, the exosomes are from the subject to be treated. In a particular embodiment, the exosomes are administered to the bloodstream of the subject by injection. In a particular embodiment, the method further comprises isolating the exosomes from a biological sample from the subject and adding the compound to the exosomes.

In accordance with another aspect of the instant invention, compositions for practicing the above methods are also provided.

DETAILED DESCRIPTION OF THE INVENTION

Adipose signaling has historically been ascribed to the endocrine effects of adipokines, which can elevate systemic inflammation. Recently, adipose has been identified as a direct source of disease signaling via exosomal miRNA communication, linking adipose signaling to cardiometabolic health in peripheral tissues (such as skeletal muscle) with a novel inter-organ mechanism (Ferrante, et al., Pediatr. Res. (2015) 77: 447-54; Hubal, et al., Obesity (2017) 25:102-10). Adipocytes are the source of as much as 60% of circulating exosomes and a wide tissue distribution of these exosomes to liver, muscle, brain, and other organs has been discovered (Ferrante, et al., Pediatr. Res. (2015) 77: 447-54; Hubal, et al., Obesity (2017) 25:102-10; Thomou, et al., Nature (2017) 542:450-455). Indeed, adipose exosomes deliver their RNA and protein cargo to most organs in the body (Thomou, et al., Nature (2017) 542:450-455). Significantly, adipocyte-derived exosomes are taken up and functional in multiple tissues and cells (e.g., hepatocytes, myocytes, leukocytes, fibroblasts, etc.) (Ferrante, et al., Pediatr. Res. (2015) 77:447-54; Koeck, et al., J. Surg. Res. (2014) 192:268-75).

Exosomes are actively shed nanoparticle-sized endocytic vesicles that transport lipids, sugars, nucleic acids, and proteins between cells, even over long distances (see, e.g., Camussi et al., Am. J. Cancer Res. (2011) 1(1): 98-110; Zernecke et al., Sci. Signal (2009) 2(100):ra81; Thery, C., F1000 Biol. Rep. (2011) 3:15). Adipose exosomal signaling is largely determined by their microRNA content, which can control gene expression in target cells by inhibiting mRNA translation or enhancing mRNA degradation (see, e.g., Karelis et al., J. Clin. Endocrinol. Metab. (2004) 89(6): 2569-75; Bartel, Cell (2009) 136(2): 215-33; Thomou, et al., Nature (2017) 542:450-455; Deng, et al., Diabetes (2009) 58:2498-2505). Therefore, exosomes may contribute to mechanisms by which adipocytes (and adipose tissue) in obese individuals can induce dysfunction in other organ systems (see, e.g., Kishida et al., Ann. Med. (2012) 44(3): 233-41; Camussi et al., Am. J. Cancer Res. (2011) 1(1): 98-110; Zernecke et al., Sci. Signal (2009) 2(100): ra81; Thomou, et al., Nature (2017) 542:450-455). For example, injection of adipose tissue exosome-like vesicles from obese mice into lean mice evokes insulin resistance (Deng, et al., Diabetes (2009) 58:2498-2505).

Exosomes can be used to deliver nucleic acids for therapeutic purposes (Xin et al., Stroke (2017) 48:A156; Li et al., Circulation (2017) 136:A19193). Artificial exosomes (or liposomes) can be used as delivery vehicles for therapeutic nucleic acids (Garcia-Manrique, et al., Trends Biotechnol.

(2018) 36:10-14). However, many problems (e.g. toxicities) have been associated with synthetic or cell line-derived exosomes (Stanley, S., Curr. Opin. Biotech. (2014) 28:69-74). Here, it is shown that an individual's own exosomes can be used as a nucleic acid delivery vector. As explained above, adipocyte-derived exosomes (nanoparticle-sized endocytic vesicles constitutively-released by fat tissue in all humans) readily deliver their RNA cargo to most organs in the body (Ferrante, et al., Pediatr. Res. (2015) 77: 447-54; Hubal, et al., Obesity (2017) 25:102-10; Koeck, et al., J. Surg. Res. (2014) 192: 268-75; Thomou, et al., Nature (2017) 542:450-455). Therefore, a generalizable platform for personalized treatment using a patient's own exosomes to deliver a missing gene product(s) (e.g., mRNA) is provided.

In accordance with the instant invention, methods for delivering a compound to a cell and/or subject are provided. The delivery can be in vitro, in vivo, or ex vivo. The method comprises contacting the cells with exosomes containing the compound. In a particular embodiment, the method comprises isolating adipocyte-derived exosomes (e.g., from a biological sample (e.g., blood or urine) from a subject to be treated); delivering (e.g., transfecting) a therapeutic compound (e.g., a gene product, a protein, or nucleic acid (e.g., RNA, DNA, mRNA, cDNA, siRNA, miRNA, long non-coding RNAs (lncRNA) etc.)); and administering (e.g., intravenously) the exosomes to the subject (e.g., at certain doses and intervals to maintain adequate tissue levels of the therapeutic compound). In a particular embodiment, the exosomes are adipocyte-derived exosomes. In a particular embodiment, the exosomes cross a biological membrane such as the blood brain barrier. In a particular embodiment, the exosomes are administered to a subject intravenously.

Examples of methods for isolating adipocyte-derived exosomes are provided in WO 2016/201220 (incorporated herein by reference). According to one aspect of the instant invention, the method for isolating adipocyte-derived exosomes comprises obtaining a biological sample from a subject which contains adipocyte-derived exosomes; and isolating the adipocyte-derived exosomes from the biological sample using a binding agent which binds to at least one marker specific for adipocyte-derived exosomes. In a particular embodiment, the exosomes are isolated from a biological sample obtained from the subject to be treated. In a particular embodiment, the exosomes are isolated from a biological sample obtained from one or more subjects (e.g., pooled samples from subjects other than the one to be treated). In a particular embodiment, the exosomes may be isolated from a freshly collected biological sample (e.g., not frozen). In a particular embodiment, the exosomes may be isolated from a biological sample that has been frozen and/or refrigerated. Biological samples may be clarified before exosome isolation, using, for example, a centrifugation, ultracentrifugation, filtration or ultrafiltration technique. In a particular embodiment, the exosomes may be isolated from cultured cells (e.g., a cell line). The exosome isolation procedure may also comprise additional steps, such as, for example, a density gradient purification step, an ultracentrifugation step, a filtration step, a sample concentration step, a dialysis step, a free-flow electrophoresis (FFE) step, or any combination thereof.

The exosome isolation procedure may include typical extraction techniques. For example, the procedure may include, but is not limited to, biomagnetic separation techniques, immunoprecipitation techniques, electrophoretic methods (such as polyacrylamide gel electrophoresis (PAGE), or native gel electrophoresis), chromatographic methods (such as ion exchange chromatography, size-exclusion or gel-permeation chromatography, or affinity chromatography), and fractionation methods (such as ultracentrifugation, low-pressure liquid chromatography, or solid phase extraction). In a particular embodiment, the isolation technique is a biomagnetic separation technique using bioparticles such as magnetic microspheres or magnetic nanospheres.

In a particular embodiment, the marker specific for adipocyte-derived exosomes and the binding agent form a complex (e.g., antibody-antigen or ligand-receptor). For example, the binding agent may be an antibody or antigen-binding fragment thereof specific for the adipocyte-derived exosomes marker. In some embodiments, the adipocyte-derived exosomes are isolated from other components in the biological sample using a binding agent which binds to a marker on the surface of adipocyte-derived exosomes. In certain embodiments, the marker is selectively expressed, or selectively over-expressed, on adipocyte-derived exosomes so as to allow the selective or exclusive isolation of adipocyte-derived exosomes from non-adipocyte-derived exosomes. In some embodiments, the isolated exosomes are substantially all adipocyte-derived exosomes. For example, at least 80%, at least 90%, at least 95%, at least 98%, or at least 99% of the isolated exosomes are adipocyte-derived exosomes.

Markers specific for adipocyte-derived exosomes include, without limitation: Fatty Acid Binding Protein 4 (FABP4; e.g., Gene ID: 2167), Pref-1, amino acid transporter (Asc-1), proton amino acid transporter (PAT-2), purinergic receptor 2X, ligand-gated ion channel 5 (P2RX5), leptin, EBF3, FBX031, EVA1, CD137, Shox2, Hoxc8, Hoxc9, Tbx1, Zic1, Lhx8, Tnsfrsf9, Tmem26, UCP-1, Cidea, Prdm16, N-acetyltransferase 8-like (Nat8L), prolactin receptor (PRLR), neuregulin-4 (Nrg4), transmembrane protein 120B (Tmem120B), adrenergic 03 receptor (Adrb3), aquaporin-7 (Aqp7), G protein-coupled receptor 81 (Grpr81), G protein-coupled receptor 119 (Gpr119), fatty acid transporter (SLC27a1/FATP1), solute carrier family 7 member 10 (SLC7a10/Asc-1 neutral amino acid transporter), mitochondrial protein uncoupling protein-1 (UCP-1), CD300LG, tetraspanin 18 (tspan18), and frizzled-4 (Fzd4). Such markers are described, for example, in Ussar et al., Sci. Transl. Med. (2014) 6(24):247ra103 (the entirety of which is incorporated by reference herein). In a particular embodiment, the adipocyte-derived exosomes marker is FABP4. In a particular embodiment, the binding agent is an anti-FABP4 antibody or antigen-binding fragment thereof.

The binding agent may be, for example, an antibody or an antigen-binding fragment thereof, an aptamer, or a fusion protein containing a binding moiety to at least one of the adipocyte-derived exosome markers (e.g., an FABP4 binding moiety), or a binding moiety of any one of the markers described herein. The binding agent may be used in conjunction with other components to facilitate isolation of exosomes, such as a bioparticle or by utilizing avidin/streptavidin interactions. Examples of bioparticles include, without limitation: a magnetic bead or an agarose bead. Examples of magnetic beads include, without limitation: a sepharose magnetic bead, a streptavidin magnetic bead, Protein A magnetic bead, Protein G magnetic bead, a ferromagnetic bead, a magnetic nanosphere, a magnetic microsphere, and a polyvinyl alcohol magnetic particle (M-PVA Magnetic Bead). For example, the binding agent may be conjugated directly or indirectly to the bioparticle. Where magnetic beads are used, bound exosomes may then be collected using a magnet. The isolated, bead-bound exosomes may then be re-suspended in an appropriate buffer.

Where the binding agent is an antibody, it may be, for example, a human antibody, a mouse antibody, a rat antibody, a domestic fowl (e.g., chicken) antibody, a rabbit antibody or a goat antibody. It may also be a polyclonal or monoclonal antibody, or a variant or fragment thereof (such as an F(ab')2, Fab', Fab or Fv fragment). The antibody may also be chimeric, humanized, or completely human.

In a particular embodiment, the binding agent comprises an anti-FABP4 antibody or an antigen-binding fragment thereof. In a particular embodiment, the adipocyte-derived exosomes are isolated using magnetic beads. In a particular embodiment, the isolated adipocyte-derived exosomes are substantially free of other non-adipocyte-derived exosomes.

A biological sample refers to a sample obtained from a subject. The biological sample may comprise cells or may be cell free. Examples of biological samples include, without limitation: blood, sputum, saliva, tissue, stool, urine, serum, cerebrospinal, cells, secretions or the like. Where the sample is a tissue, the tissue sample can be obtained by biopsy. The biological sample can also be obtained by a minimally invasive method, such as a swab, or a non-invasive sampling method, such as a urine sample can be obtained and used in the methods of the disclosure. The swab, for example, can be obtained from any part of the body such as the mouth. In a particular embodiment, the biological sample is urine.

In a particular embodiment, the biological sample is not adipose tissue. In a particular embodiment, the biological sample is a biological fluid. Examples of biological fluids include, without limitation: milk, blood, serum, plasma, ascites, cyst fluid, pleural fluid, peritoneal fluid, cerebrospinal fluid, tears, urine, saliva, sputum, or combinations thereof. In a particular embodiment, the biological sample is blood, serum, or urine. In a particular embodiment, the biological sample is blood or serum. In a particular embodiment, the biological sample is urine. Generally, urine samples yield similar quality but larger quantities of adipocyte-derived exosomes than serum samples.

An example of isolating adipocyte-derived exosomes from urine and blood/plasma is provided in WO 2016/201220. Briefly, blood/plasma and urine samples were obtained from human subjects. To selectively isolate adipocyte-derived exosomes, exosomes in the blood/serum or urine sample were first precipitated using the ExoQuick®-TC Exosome Precipitation Solution (System Biosciences, Mountain View, CA). Blood/serum or urine sample were optionally centrifuged at 3000×g (6066 rpm on a benchtop centrifuge, r=7.3 cm) for 15 minutes to remove cells and cellular debris. The supernatant was harvested and then added to the ExoQuick®-TC Exosome Precipitation solution. The resulting mixture was mixed thoroughly and incubated for at least 12 hours at 4° C. Following this incubation, the mixture was centrifuged (1500×g for 30 minutes) and the supernatant was discarded. The pellet was again centrifuged (1500×g for 5 minutes) and excess supernatant was removed (so as to leave about 100 µl of supernatant with the pellet). The pellet was then re-suspended in Phosphate-Buffered Saline (PBS) (by adding about 100 µl PBS). A positive-selection cocktail was produced for the EasySep® "Do-It-Yourself" Selection Kit, in accordance with the manufacturer's directions, using an antibody specific for Fatty Acid Binding Protein 4 (FABP4). The positive-selection cocktail was then added to the PBS-exosome suspension, mixed, and incubated (15 minutes). After this incubation, EasySep® Magnetic Nanoparticles were added and mixed to ensure a uniform suspension. After a short incubation (10 minutes), the suspension was diluted with PBS (2 mL) and the tube containing the suspension was placed beside a magnet to localize the magnetic beads to the inside surface of the tube. The supernatant was then removed, thereby removing non-magnetically-labeled material. The tube was then removed from the magnet and the magnetic beads in the tube were suspended in PBS. This magnetic selection step was then repeated an additional two times. After these magnetic selection steps, a substantially pure population of adipocyte-derived exosomes was obtained.

The exosomes of the instant invention, e.g., adipocyte-derived exosomes, may be loaded with the compound(s) to be delivered to the cell or subject by any of many possible techniques known in the art. For example, the compounds can be inserted into the exosomes by microinjection, calcium phosphate or calcium chloride co-precipitation, DEAE-dextran mediated transfection, detergent exposure, poly-L-lysine, Lipofectamine™, Exo-Fect™ (System Biosciences; Palo Alto, CA), electroporation, viral transduction or transfection, and the like. In a particular embodiment, the compounds are introduced into the exosomes by transfection. In a particular embodiment, the compounds are introduced into the exosomes by electroporation.

The compound(s) of the exosomes can be, without limitation: a biological agent (a biologic), detectable agents (e.g., imaging agents or contrast agents), or therapeutic agent (Lassar et al., Expert Opin. Biol. Ther. (2015) 15:103-17). Such compounds include, without limitation: polypeptides, peptides, glycoproteins, nucleic acids (e.g., DNA, cDNA, RNA, mRNA, oligonucleotides, plasmids, RNA interference (RNAi) (e.g., siRNA, ssRNA, and shRNA), antisense oligonucleotides, microRNA (miRNA), lncRNA, mimics, etc.), ribozymes, synthetic and natural drugs, polysaccharides, antibodies or antigen-binding fragments thereof, small molecules, lipids, peptidomimetics, and the like. The compound may be composed of sugars, proteins, or nucleic acids or complex combinations of these substances, or may be living entities such as cells and tissues. In a particular embodiment, the compound is a vaccine, an allergenic, gene therapy, tissue, or recombinant therapeutic protein. In a particular embodiment, the compound is a therapeutic agent such as a therapeutic protein or a nucleic acid (e.g., DNA or RNA) encoding the therapeutic protein. In a particular embodiment, the compound is a nucleic acid molecule (e.g., RNAi or microRNA). In a particular embodiment, the nucleic acid comprises transcriptional and translational control sequences, such as promoters, enhancers, translational start signals (e.g., ATG or AUG codons), polyadenylation signals, terminators, and the like, and which facilitate the expression of a nucleic acid or a polypeptide coding sequence in a host cell or organism. The nucleic acid may be an isolated nucleic acid molecule or contained within a vector, particularly an expression vector. In a particular embodiment, the contents of the exosomes (e.g., microRNA) are removed prior to addition of the compound. The compound may be isolated from a variety of natural sources such as human, animal, or microorganism. Alternatively, the compound may be produced by biotechnology methods and/or other known technologies in the field.

In accordance with another aspect of the instant invention, compositions comprising the exosomes comprising a desired compound(s) (e.g., loaded adipocyte-derived exosomes) and at least one pharmaceutically acceptable carrier are provided. The compositions of the instant invention may further comprise other therapeutic agents.

In accordance with another aspect of the instant invention, methods for preventing, inhibiting, and/or treating a disease or disorder in a subject are provided. In a particular embodiment, the methods comprise isolating exosomes (e.g., adipocyte-derived exosomes) from a biological sample from a subject (particularly the subject to be treated), adding the compound (e.g., therapeutic agent) to the exosomes, and administering the compound-containing exosomes to the subject, thereby preventing, inhibiting, and/or treating the disease or disorder. The methods optionally comprise obtaining the biological sample from the subject. In a particular embodiment, the method comprises isolating adipocyte-derived exosomes (e.g., from a biological sample (e.g., blood or urine) from a subject to be treated); delivering (e.g., transfecting) a compound (e.g., a gene product such as a protein or nucleic acid (e.g., RNA, DNA, mRNA, cDNA, etc.)) of a missing or defective gene in the subject; and administering (e.g., intravenously) the exosomes to the subject (e.g., at certain doses and intervals to maintain adequate tissue levels of functional protein or gene product). In a particular embodiment, the compound/therapeutic agent is a translatable nucleic acid molecule (e.g., mRNA). The use of translatable mRNA (as opposed to protein) is advantageous in that a sustained amplification effect can be expected in the resulting protein (Sullenger, et al., Science (2016) 352:1417-20).

The compositions of the instant invention can be administered to an animal, in particular a mammal, more particularly a human, in order to treat, inhibit, or prevent the disease or disorder. The compositions of the instant invention may also comprise at least one other therapeutic agent for treating, inhibiting, or preventing the disease or disorder. The additional therapeutic agent may also be administered in a separate composition from the exosomes of the instant invention. The compositions may be administered at the same time and/or at different times (e.g., sequentially).

In a particular embodiment of the instant invention, the exosomes comprise at least one therapeutic protein and/or nucleic acid encoding a therapeutic protein. A therapeutic protein effects amelioration and/or cure of a disease, disorder, pathology, and/or the symptoms associated therewith. Therapeutic proteins include, without limitation: enzymes, antibodies, hormones, growth factors, other polypeptides. Exosomes are particularly attractive for treatment of inborn errors of metabolism due to defects in ubiquitously expressed genes. In a particular embodiment, the therapeutic protein is a protein used in enzyme replacement therapy.

Examples of disease or disorders to be treated by the methods of the instant invention include, without limitation: diabetes (e.g., type 2 diabetes), alpha-1 antitrypsin deficiency, NAGS deficiency (NAGSD) or hyperammonemia, neurological disorders (e.g., neurological disorders of the central nervous system) such as neurodegenerative disorders, metabolic disorders, inflammatory disorders, metabolic disorders, and lysosomal storage diseases (LSDs; such as, without limitation, Gaucher's disease, Pompe disease, Niemann-Pick, Hunter syndrome (MPS II), Mucopolysaccharidosis I (MPS I), GM2-gangliosidoses, Gaucher disease, Sanfilippo syndrome (MPS IIIA), Tay-Sachs disease, Sandhoff's disease, Krabbe's disease, metachromatic leukodystrophy, and Fabry disease). Lysosomal storage diseases are generally inherited genetic defects that result in an enzyme deficiency, which prevents cells from performing their natural recycling function. Various enzymes implicated in lysosomal storage diseases or enzymes that can fulfill the function of the deficient enzymes can be delivered using the methods of the present invention. In a particular embodiment, the disease or disorder is a single gene disease or disorder (i.e., when a certain gene is known to cause a disease or disorder). In a particular embodiment, the disease is characterized by a single defective or missing gene such that replacement with RNA and/or protein treats the disease or disorder (e.g., a replacement therapy). In a particular embodiment, the disease or disorder is Niemann Pick disease. In a particular embodiment, the disease or disorder is alpha-1 antitrypsin deficiency.

Examples of specific therapeutic proteins (or nucleic acids encoding the therapeutic protein) and the disease or disorder to be treated include, without limitation: alpha-galactosidase, agalsidase beta, or agalsidase alfa for Fabry disease; SERPINA1 (alpha-1-antitrypsin) for alpha-1 antitrypsin deficiency; N-acetylglutamate synthase (NAGS) for NAGS deficiency (NAGSD) or hyperammonemia; glucocerebrosidase, imiglucerase, taliglucerase alfa, velaglucerase alfa, or alglucerase for Gaucher disease; iduronidase or laronidase for mucopolysaccharidoses (MPS) I; iduronate-2-sulfatase or idursulfase for MPS II; N-acetylgalactosamine-6-sulfatase or elosulfase alpha for MPS IV; arylsulfatase B or galsulfase for MPS VI; alpha-glucosidase or alglucosidase alpha for Pompe disease; and Niemann-Pick disease, type C1 (NPC1; NPC intracellular cholesterol transporter 1; see, e.g., PubMed Gene ID: 4864) or acid sphingomyelinase for Niemann-Pick disease. In a particular embodiment, the disease or disorder is Niemann-Pick disease. In a particular embodiment, the disease or disorder is Niemann-Pick disease and the compound of the exosomes is Niemann-Pick disease, type C1 (NPC1) or a nucleic acid molecule encoding NPC1 (e.g., a DNA molecule or an RNA molecule (e.g., mRNA)).

The exosomes described herein will generally be administered to a patient or subject as a pharmaceutical preparation. The term "patient" as used herein refers to human or animal subjects. These exosomes may be employed therapeutically, under the guidance of a physician or other healthcare professional.

The pharmaceutical preparation comprising the exosomes of the invention may be conveniently formulated for administration with an acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of exosomes in the chosen medium will depend on the hydrophobic or hydrophilic nature of the medium, as well as the size, enzyme activity, and other properties of the exosomes. Solubility limits may be easily determined by one skilled in the art.

As used herein, "pharmaceutically acceptable medium" or "carrier" includes any and all solvents, dispersion media and the like which may be appropriate for the desired route of administration of the pharmaceutical preparation, as exemplified in the preceding discussion. The use of such media for pharmaceutically active substances is known in the art. Except insofar as any conventional media or agent is incompatible with the exosome to be administered, its use in the pharmaceutical preparation is contemplated.

The dose and dosage regimen of the exosomes according to the invention that is suitable for administration to a particular patient may be determined by a physician considering the patient's age, sex, weight, general medical condition, and the specific condition for which the exosomes are being administered and the severity thereof. The physician may also take into account the route of administration of the exosomes, the pharmaceutical carrier with which the exosomes are to be combined, and the exosomes' biological activity.

Selection of a suitable pharmaceutical preparation will also depend upon the mode of administration chosen. For example, the exosomes of the invention may be administered by injection into the bloodstream or intravenously. In these instances, the pharmaceutical preparation comprises the exosomes dispersed in a medium that is compatible with the site of injection.

Exosomes may be administered by any method such as intranasal, intramuscular, subcutaneous, oral, or intravenous injection into the blood stream. Pharmaceutical preparations for injection are known in the art. If injection is selected as a method for administering the exosomes, steps must be taken to ensure that sufficient amounts of the exosomes reach their target cells to exert a biological effect. The lipophilicity of the exosomes, or the pharmaceutical preparation in which they are delivered, may be increased so that the molecules can arrive at their target location. Methods for increasing the lipophilicity of a molecule are known in the art.

Pharmaceutical compositions containing the exosomes of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous. Injectable suspensions may be prepared, for example, using appropriate liquid carriers, suspending agents and the like.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art. Appropriate concentrations for alleviation of a particular pathological condition may be determined by dosage concentration curve calculations, as known in the art.

In accordance with the present invention, the appropriate dosage unit for the administration of exosomes may be determined by evaluating the toxicity of the molecules in animal models. Various concentrations of exosome pharmaceutical preparations may be administered to mice, and the minimal and maximal dosages may be determined based on the beneficial results and side effects observed as a result of the treatment. Appropriate dosage unit may also be determined by assessing the efficacy of the exosomes treatment in combination with other standard drugs. The dosage units of exosomes may be determined individually or in combination with each treatment according to the effect detected.

The pharmaceutical preparation comprising the exosomes may be administered at appropriate intervals until the pathological symptoms are reduced or alleviated, after which the dosage may be reduced to a maintenance level. The appropriate interval in a particular case would normally depend on the condition of the patient.

Definitions

The following definitions are provided to facilitate an understanding of the present invention:

The singular forms "a," "an," and "the" include plural referents unless the context clearly dictates otherwise.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., polysorbate 80), emulsifier, buffer (e.g., Tris HCl, acetate, phosphate), antimicrobial, bulking substance (e.g., lactose, mannitol), excipient, auxiliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions may be employed as carriers, particularly for injectable solutions. Suitable pharmaceutical carriers are described in "Remington's Pharmaceutical Sciences" by E. W. Martin (Mack Publishing Co., Easton, PA); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients, American Pharmaceutical Association, Washington.

As used herein, the term "small molecule" refers to a substance or compound that has a relatively low molecular weight (e.g., less than 4,000, less than 2,000, particularly less than 1 kDa or 800 Da). Typically, small molecules are organic, but are not proteins, polypeptides, or nucleic acids, though they may be amino acids or dipeptides.

The term "treat" as used herein refers to any type of treatment that imparts a benefit to a patient afflicted with a disease, including improvement in the condition of the patient (e.g., in one or more symptoms), delay in the progression of the condition, etc.

As used herein, the term "prevent" refers to the prophylactic treatment of a subject who is at risk of developing a condition resulting in a decrease in the probability that the subject will develop the condition.

As used herein, the term "subject" refers to an animal, particularly a mammal, particularly a human.

A "therapeutically effective amount" of a compound or a pharmaceutical composition refers to an amount effective to prevent, inhibit, treat, or lessen the symptoms of a particular disorder or disease. The treatment of a disease or disorder herein may refer to curing, relieving, and/or preventing the disease or disorder, the symptom(s) of it, or the predisposition towards it.

As used herein, the term "therapeutic agent" refers to a chemical compound or biological molecule including, without limitation, nucleic acids, peptides, proteins, and antibodies that can be used to treat a condition, disease, or disorder or reduce the symptoms of the condition, disease, or disorder.

As used herein, the term "purified" or "to purify" refers to the removal of contaminants or undesired compounds from a sample or composition. For example, purification can result in the removal of from about 70 to 90%, up to 100%, of the contaminants or undesired compounds from a sample or composition. In certain embodiments, at least 90%, 93%, 95%, 96%, 97%, 98%, 99%, 99.5%, or more of undesired compounds from a sample or composition are removed from a preparation.

The term "isolated" refers to the separation of a compound from other components present during its production or from its natural environment. "Isolated" is not meant to exclude artificial or synthetic mixtures with other compounds or materials, or the presence of impurities that do not substantially interfere with the fundamental activity, and that may be present, for example, due to incomplete purification, or the addition of stabilizers.

An "antibody" or "antibody molecule" is any immunoglobulin, including antibodies and fragments thereof, that binds to a specific antigen. As used herein, antibody or antibody molecule contemplates intact immunoglobulin molecules, immunologically active portions of an immunoglobulin molecule, and fusions of immunologically active portions of an immunoglobulin molecule. The term "antibody" includes, but is not limited to, polyclonal antibodies, multiclonal antibodies, monoclonal antibodies, chimeric antibodies, humanized and primatized antibodies, human antibodies, recombinantly produced antibodies, intrabodies, multispecific antibodies, bispecific antibodies, monovalent antibodies, multivalent antibodies, anti-idiotypic antibodies, synthetic antibodies, including muteins and variants thereof; antibody fragments such as Fab fragments, F(ab') fragments, single-chain FvFcs, single-chain Fvs; and derivatives thereof including Fc fusions and other modifications, and any other immunologically active molecule so long as they exhibit the desired biological activity (i.e., antigen association or binding). Moreover, the term further includes all classes of antibodies (i.e. IgA, IgD, IgE, IgG, and IgM) and all isotypes (i.e., IgG1, IgG2, IgG3, IgG4, IgA1, and IgA2), as well as variations thereof unless otherwise dictated by context.

As used herein, the term "immunologically specific" refers to proteins/polypeptides, particularly antibodies, that bind to one or more epitopes of a protein or compound of interest, but which do not substantially recognize and bind other molecules in a sample containing a mixed population of antigenic biological molecules.

As used herein, a "biological sample" refers to a sample of biological material obtained from a subject, particularly a human subject, including a tissue, a tissue sample, cell(s), and a biological fluid (e.g., blood or urine).

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a separated DNA molecule or a DNA molecule inserted into a vector, such as a plasmid or virus vector.

A "vector" is a genetic element, such as a plasmid, cosmid, bacmid, phage or virus, to which another genetic sequence or element (either DNA or RNA) may be attached. The vector may be a replicon so as to bring about the replication of the attached sequence or element. An "expression vector" is a vector which facilitates the expression of a nucleic acid or a polypeptide coding sequence in a host cell or organism. The expression vector may comprise nucleic acid segments that possess transcriptional and translational control sequences, such as promoters, enhancers, translational start signals (e.g., ATG or AUG codons), polyadenylation signals, terminators, and the like, and which facilitate the expression of a nucleic acid or a polypeptide coding sequence in a host cell or organism.

The following example describes illustrative methods of practicing the instant invention and is not intended to limit the scope of the invention in any way.

EXAMPLE

N-acetylglutamate synthase (NAGS) is critical for urea cycle function and catalyzes the formation of N-acetylglutamate (NAG), a unique and essential allosteric activator of carbamyl phosphate synthetase 1 (CPS1), the first and rate-limiting enzyme of ureagenesis (Caldovic, et al., Biochem. J. (2003) 372:279-290; Mew et al., Appl. Clin. Genet. (2011) 4:127-135). NAG is produced in the mitochondrial matrix of the liver and small intestine and plays an important role in regulating urea production (Caldovic, et al., Biochem. J. (2003) 372:279-290). Primary or secondary NAGS deficiency (NAGSD) or insufficiency causes hyperammonemia (Mew et al., Appl. Clin. Genet. (2011) 4:127-135).

The NAGS knockout mouse model (koNAGS) of hyperammonemia can be rescued by two small molecule supplements—N-carbamyl-L-glutamate (NCG) and citrulline (Cit) (Caldovic, et al., J. Pediatr. (2004) 145:552-4). With the supplementation, the mice can be reared to adulthood and can reproduce to generate exclusively koNAGS homozygous progeny (Senkevitch, et al., Mol. Genet. Metab. (2012) 106:160-8). Indeed, the survival rate of koNAGS homozygous mice was 85% when they were given intra-peritoneal injections with NCG and Cit beginning at birth and continuing until weaning, followed by supplementation in their drinking water thereafter. Withdrawal of the rescue chemicals results in the death of the mice within 24-48 hours (Senkevitch, et al., Mol. Genet. Metab. (2012) 106:160-8). Because the mice remain healthy until withdrawal of NCG and Cit, these mice are an ideal model of hyperammonemia. For example, it can be tested whether a gene product delivered via exosomes results in functional protein in healthy koNAGS mice and whether it will rescue the mice once the chemicals have been withdrawn.

As explained herein, a generalizable platform for personalized treatment using a patient's own exosomes to deliver a missing gene product(s) is provided. This platform comprises several steps—isolation, transfection, and delivery. The steps of this generalizable platform are provided with regard to NAGS deficiency hyperammonemia.

Fatty acid binding protein 4 (FABP4) can be used as a sensitive and specific marker for adipocyte-derived exosomal isolation from body fluids (Ferrante, et al., Pediatr. Res. (2015) 77:447-54; Furuhashi, et al., Clin. Med. Insights Cardiol. (2014) 8:23-33). Briefly, exosomes can be isolated from serum using an exosome precipitant solution and then resuspended in PBS. Commercially available antibody complexes and dextran-coated magnetic particles were used to bind FABP4+ exosomes. The anti-FABP4-antibody complexes link targeted exosomes to magnetic particles and labeled exosomes were positively-selected when placed near a magnet. Isolated adipocyte-derived exosomes have been characterized for FABP4, Pref-1, and CD14 (Ferrante, et al., Pediatr. Res. (2015) 77:447-54; WO 2016/201220). Almost all adipocyte exosomes were FABP4+(Ferrante, et al., Pediatr. Res. (2015) 77:447-54; WO 2016/201220).

Exosomes can be isolated, for example, from visceral adipose tissue (VAT) (Ferrante, et al., Pediatr. Res. (2015) 77:447-54; Deng, et al., Diabetes (2009) 58:2498-2505). Briefly, VAT can be excised from euthanized koNAGS mice (e.g., 24-30 weeks old; n=100) and cut into sections (e.g., 3 mm$^3$). Sections can be incubated in low glucose DMEM with pyruvate for one hour at 37° C. VAT and remaining media, containing exosomes, can then be removed and the media subsequently filtered. Exosomes can be isolated from the media using ExoQuick®-TC (System BioSciences; 200 µl per 1 mL media) and resuspended in PBS.

The coding sequence of the mouse N-acetylglutamate synthase (NAGS) gene (e.g., PubMed Gene ID: 162417; GenBank Accession Nos. NM_153006.2 and NP_694551.1) was codon-optimized for expression in mice using OptimumGene™ (GenScript, Piscataway, NJ). The 3' UTR includes Woodchuck post-transcriptional response element (WPRE), which can create a tertiary structure enhancing expression. The 5' UTR includes a Kozak consensus sequence, which facilitates the initiation of translation.

Figure 1:
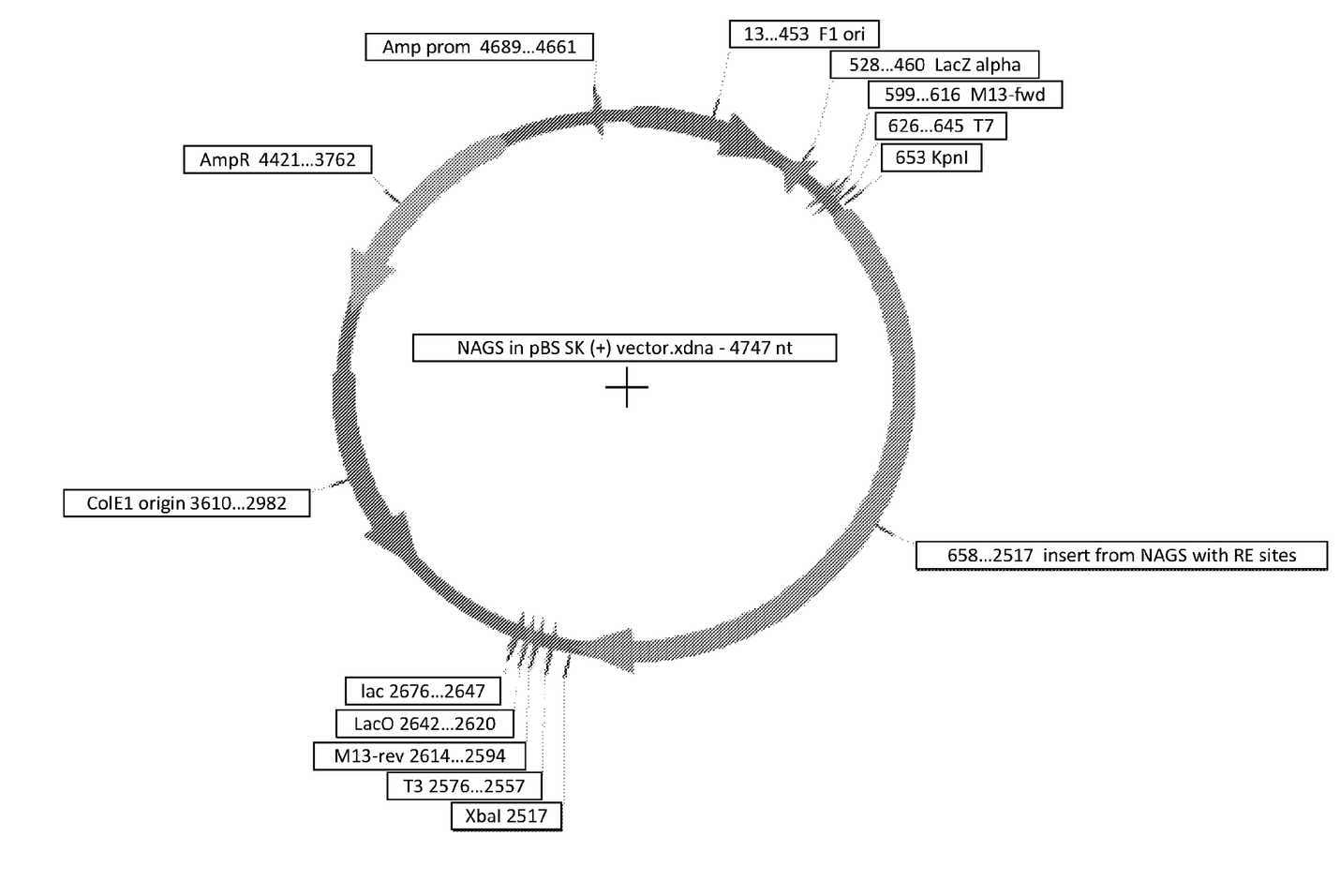
FIG. 1 provides a schematic of the pBluescript II SK(+) cloning vector containing a full-length, codon-optimized N-acetylglutamate synthase (NAGS) gene and a T7 phage promoter site to enable transcription.

Gene Runner software was used to verify that there are no splice variants or premature stop codons within the insert. The pBlueScript II SK (+) vector was chosen because it contains a T7 RNA polymerase promoter site to enable in vitro transcription. The vector is grown in *E. coli* under standard conditions. The T3 promoter may be used to transcribe the nonfunctional antisense strand of the insert (e.g., as a control following the same process). SerialCloner 2-6-1 software was used to confirm proper orientation of the NAGS insert within the pBlueScript II SK (+) vector. Sanger sequencing can be used to confirm that the NAGS sequence has not mutated. FIG. 1 provides a schematic of the vector.

The vector can be linearized and full-length mRNA can be synthesized via in vitro transcription using the mMESSAGE mMACHINE® T7 ULTRA Transcription Kit (ThermoFisher Scientific, Waltham, MA). This process includes addition of poly(A)-tail and an anti-reverse cap analog, both of which increase stability of the mRNA product and increases protein yield (Pascolo, S. (2008) Vaccination with Messenger RNA (mRNA). In: Bauer et al. (eds) Toll-Like Receptors (TLRs) and Innate Immunity. Handbook of Experimental Pharmacology, vol 183. Springer, Berlin, Heidelberg).

Adipocyte-derived exosome have been co-culture with HepG2 cells (Koeck, et al., J. Surg. Res. (2014) 192:268-75). Briefly, HepG2 cells were cultured to 75% confluence and exposed to PKH26-labeled adipocyte-derived exosomes from obese or lean donors for 48 hours. After exposure to the exosomes, red fluorescence was seen in a perinuclear pattern in the HepG2 cells. No red fluorescence was present in cells exposed to control media without exosomes.

The effect of adipocyte-derived exosomes from obese vs. lean subjects on THP-1 macrophage cholesterol efflux gene expression has been shown (WO 2016/201220). Briefly, THP-1 cells were incubated with obese and lean visceral adipose-derived exosomes for 24 hours. ABCA1, CYP27A1, ABCG1, PPARγ, and LXRα were measured using qRT-PCR. ABCA1 and CYP27A1 were significantly downregulated in response to exosome exposure, providing evidence of functional delivery of RNA contents.

Exosomes can be transfected with mouse NAGS mRNA using the Exo-Fect™ Exosome Transfection Kit (System BioSciences). Briefly, adipocyte-derive exosomes (e.g., ~1×10$^7$ as determined by protein content) can be incubated with NAGS mRNA (e.g., 1 µg) and transfection reagent at 37° C. for 10 minutes. The reaction can be stopped by placing samples on ice. Successful exosome transfection of NAGS mRNA can be confirmed via real-time PCR.

koNAGS mice (e.g., 8-10 weeks old; n=8) can be anesthetized (e.g., with ketamine (80 mg/kg) and xylazine (5 mg/kg), followed by opening of the body cavity and perfusion of the livers with a solution of collagenase. These murine koNAGS hepatocytes, which contain no endogenous NAGS, can be used for in vitro studies. Primary koNAGS hepatocytes (e.g., ~6×10$^5$) can be plated per well in a 24-well plate. Following overnight recovery, hepatocytes can be exposed to NAGS mRNA-transfected adipocyte-derived exosomes across a range of concentrations (e.g., 0.1, 0.3, 1, 3, 10, 30 µg/mL of adipocyte-derived exosomes) along with appropriate controls such as media control and adipocyte-derived exosomes. Hepatocyte NAGS mRNA and protein levels can be measured 24 hours later by, for example, quantitative PCR and species-specific ELISA, respectively. Urea and urea cycle intermediates can be measured in the media. NAGS mRNA-transfected adipocyte-derived exosomes will lead to sustained expression of hepatocyte NAGS in a concentration-dependent manner. Further, restored urea cycle function will be sustained concordantly (e.g. increased urea concentration in the culture media).

WT mice and koNAGS mice (e.g., 8-10 weeks old) can be entered into one of four experimental groups (e.g., n=10 mice/group/dose): 1) vehicle/WT, 2) exosomes/WT, 3) vehicle/koNAGS, and 4) exosomes/koNAGS. Body mass can be measured for each mouse at the start and end of the study. Exosomes transfected with NAGS mRNA can be administered via tail vein injection (e.g., in four doses) to reach concentrations in the circulation approximating the most efficacious in vitro concentrations. Approximately 100-150 µL of suspension containing exosomes can be injected into the tail vein of koNAGS mice and their WT littermates. PBS, used to suspend the exosomes, can be used as a vehicle. This procedure can be performed on un-anesthetized mice. Prior to the injection, the mouse can be exposed to a heat lamp to dilate the tail vein. During the injection, the mice can be placed in a restrainer permitting access to the tail vein. The tail can be cleansed with 70% ethanol and the injection can be made in the tail vein using 27-gauge needle.

NCG and Cit supplementation can be withdrawn (e.g., 24 hours) after injection of the exosome suspension. After withdrawal of NCG and Cit supplementation (e.g., 24 hours), mice can be euthanized and necropsied to obtain blood, liver and other tissues for biochemical and molecular analyses. For the range of doses, tissue distribution can be assessed, deriving a minimal dose and fractional delivery to the target tissue (liver) in koNAGS mice. Initial efficacy of endogenous transfected exosomal delivery to both wild-type and koNAGS mice can be determined. NAGS mRNA-transfected adipocyte-derived exosomes will lead to sustained expression of liver NAGS in a dose-dependent manner. Liver NAGS protein and mRNA levels can be measured, for example, by species-specific ELISA and quantitative PCR, respectively. Restored urea cycle function will also be sustained concordantly. Ammonia and other urea cycle intermediates can be measured in the serum. These in vivo experiments can be the foundation for further studies including formal good laboratory practice (GLP) studies including formal pharmacokinetics, dose-ranging (multiple ascending dose (MAD)) and no-observed-adverse-effect level (NOAEL) studies in the koNAGS model.

A number of publications and patent documents are cited throughout the foregoing specification in order to describe the state of the art to which this invention pertains. The entire disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method of treating a disease in a subject, said method comprising
isolating fatty acid binding protein 4 (FABP4) positive, adipocyte-derived exosomes from a biological sample from said subject, wherein said isolating said FABP4 positive, adipocyte-derived exosomes from a biological sample comprises contacting the biological sample with an anti-FABP4 antibody or antigen-binding fragment thereof, and wherein the isolated adipocyte-derived exosomes are substantially free of non-adipocyte-derived exosomes,
loading the FABP4 positive, adipocyte-derived exosomes with a therapeutic agent, and
administering said FABP4 positive, adipocyte-derived exosomes containing a therapeutic agent to said subject.

2. The method of claim 1, wherein said therapeutic agent is a nucleic acid molecule.

3. The method of claim 2, wherein said nucleic acid molecule encodes a therapeutic protein.

4. The method of claim 1, wherein said disease is Niemann Pick disease and said therapeutic agent is Niemann-Pick disease, type C1 (NPC1) or a nucleic acid molecule encoding said NPC1.

5. The method of claim 1, wherein said exosomes are administered to the bloodstream of said subject by injection.

6. The method of claim 1, wherein said biological sample is urine.

7. A method of treating a disease in a subject, said method consisting of
isolating fatty acid binding protein 4 (FABP4) positive, adipocyte-derived exosomes from a biological sample from said subject by contacting the biological sample with an anti-FABP4 antibody or antigen-binding fragment thereof,
loading the FABP4 positive, adipocyte-derived exosomes with a therapeutic agent, and
administering said FABP4 positive, adipocyte-derived exosomes containing a therapeutic agent to said subject.

8. The method of claim 7, wherein said isolation of said FABP4 positive, adipocyte-derived exosomes from a biological sample by contacting the biological sample with an anti-FABP4 antibody or antigen-binding fragment thereof results in isolated adipocyte-derived exosomes substantially free of other non-adipocyte-derived exosomes.

9. The method of claim 7, wherein said therapeutic agent is a nucleic acid molecule.

10. The method of claim 9, wherein said nucleic acid molecule encodes a therapeutic protein.

11. The method of claim 7, wherein said disease is Niemann Pick disease and said therapeutic agent is Niemann-Pick disease, type C1 (NPC1) or a nucleic acid molecule encoding said NPC1.

12. The method of claim 7, wherein said exosomes are administered to the bloodstream of said subject by injection.

13. The method of claim 7, wherein said biological sample is urine.

* * * * *